(12) United States Patent
Pfaff et al.

(10) Patent No.: US 6,597,799 B1
(45) Date of Patent: Jul. 22, 2003

(54) OPTICAL DIGITAL ENVIRONMENT COMPLIANCE SYSTEM

(75) Inventors: William P. Pfaff, Navarre, FL (US); Jay Stretch, Ogden, UT (US)

(73) Assignee: Scientech, Inc., Idaho Falls, ID (US)

( * ) Notice: Subject to any disclaimer, the term of this patent is extended or adjusted under 35 U.S.C. 154(b) by 498 days.

(21) Appl. No.: 09/596,737

(22) Filed: Jun. 19, 2000

(51) Int. Cl.[7] .................................................. G06K 9/00
(52) U.S. Cl. ....................... 382/100; 382/165; 382/180; 382/224; 382/225; 382/275; 356/436; 356/438
(58) Field of Search .............................. 382/100, 162, 382/165, 225, 224, 275, 173, 180; 356/438, 436, 437

(56) References Cited

U.S. PATENT DOCUMENTS 3,841,763 A * 10/1974 Lewis .......................... 356/438
4,015,135 A * 3/1977 Tipton, Jr. .................... 250/574
6,078,681 A * 6/2000 Silver .......................... 382/133

* cited by examiner

*Primary Examiner*—Phuoc Tran
(74) *Attorney, Agent, or Firm*—Reed Smith, LLP

(57) ABSTRACT

A method and apparatus for analyzing a picture of an effluent such as a smoke plume or dust cloud to determine the opacity of the effluent. The picture of the effluent is first broken down into pixels. Each pixel corresponding to the effluent is identified and the color of each effluent pixel is analyzed to calculate the opacity of that effluent pixel. An opacity value for the entire effluent is extrapolated based on the opacity values of each effluent pixel.

31 Claims, 7 Drawing Sheets

OPTICAL DIGITAL ENVIRONMENT COMPLIANCE SYSTEM

BACKGROUND

A) Field of the Invention

This invention relates to a method and apparatus for performing a detailed analysis of digital pictures and, in particular, pictures taken of an effluent such as smoke or dust to determine the opacity of the effluent.

B) Background of Invention

The existence of pollution creates many general health concerns and the government has enacted legislation to regulate pollution levels. In particular, the government has sought to control the amounts of particulate matter in the air. Particulate matter generally refers to particles in the air that are invisible individually and visible as smoke en masse.

In order to control the distribution of these particulate matter, the Environmental Protection Agency promulgated regulations which are directed to anyone who produces smoke. These regulations require that smoke emitted into the atmosphere not exceed certain levels that have been empirically determined to be acceptable for a given operation. Under the regulations, any individual or company that produces smoke must demonstrate that the smoke levels emitted are within the established parameters to obtain a permit with their local authority.

In order to determine the amount of smoke that is output into the atmosphere, a smoke plume is analyzed to determine the opacity of the smoke plume. Opacity is generally considered to be a value of the density of the smoke.

Some devices exist that are installed within the smoke stack to measure the opacity of the smoke plumes. Referred to as Continuous Opacity Monitors ("COM"), these devices essentially utilize a light source and a photo cell detector. The light source and photo cell detector are placed at opposite walls within the smoke stack with the smoke plume in between the two. The light source directs its light toward the detector through the smoke plume. The photo cell detector measures the amount of light that passes through the smoke plume and calculates the opacity based on that percentage. The COMs, however, require difficult maintenance and may not accurately measure opacity depending on the location of light source detector in the stack and characteristics of the effluent such as water content. COMs are also expensive to replace if they break down.

Another method of measuring opacity levels of smoke plumes is for a human to visually observe the plume and estimate the opacity. The government issued a set of regulations, called Method 9 under the Environment Protection Agency Title 5, which established guidelines for the visual determination of opacity emissions from stationary resources.

Under Method 9, a qualified observer views the plume from a requisite distance away from the plume at set intervals of time. The observer then makes a subjective estimate of the percentage of opacity of the plume based on his observations and training.

In order to be an observer qualified to make opacity readings under Method 9, a person must attend a series of classes commonly known as "smoke school". In smoke school, the observer is taught the statutory guidelines and exposed to various smoke plumes to evaluate. Based on this experience, the observer becomes trained in identifying opacity levels of smoke plumes. After passing a test of these abilities, a person then qualifies to measure the opacity of smoke plumes.

Smoke plumes can differ in volume, size and color. Each case requires a different analysis regarding the opacity of the effluent. In addition, since these measurements usually occur outdoors, atmospheric conditions also affect the analysis. While a person who has had substantial experience with judging opacity for all different conditions can account for variations in the ambient conditions when making the opacity estimation, the fidelity of the results from a Method 9 visual test can be quite low since they are ultimately based on a subjection evaluation. Opacity judgements are subject to variation of human observers which allow for inconsistencies in measurements. Consequently, it would be advantageous to have a system which offered a more objective and more consistent estimation as to the opacity of the plumes.

Another disadvantage of the human visual observation technique under Method 9 is that once a observation is performed by an observer, there is no ability to repeat the estimation done by that observer. Since the plumes are not fixed in time and each observation can be made only at that specific time, the results of a visual estimation are uncheckable and unrepeatable. Accordingly, it would be advantageous to have a system whereby estimations of opacity can be checked and repeated by the same methods over any period of time.

SUMMARY OF THE INVENTION

The current invention involves a computer analysis of digital pictures taken of effluents, such as smoke plumes or dust clouds, to be able to measure opacity levels of the effluent. For smoke plumes, pictures of the plumes to be analyzed are taken and saved as image files. Each picture can be taken in conformance with the regulations established by Method 9 or any other regulatory statutes that are applicable to visual observations to estimate opacity. Each image file is then analyzed to determine the opacity of the smoke plume or dust cloud.

For each picture, the smoke must be isolated in the picture. The background to either side of the smoke is used to determine a standard against which to measure the opacity of the plume. In isolating the smoke in the picture, any artifacts must be removed in the picture. Artifacts are data in the picture file that are not relevant to the analysis. After these artifacts are removed, other phenomena different from the background of the picture must be eliminated. After these filtering processes are completed, the opacity calculation of the smoke plume can be performed by statistically analyzing the data for each pixel that corresponds to the smoke plume.

In accordance with one embodiment of the invention, a method for evaluating a picture of an effluent to determine the opacity of the effluent, comprises the steps of identifying pixels in the picture that pertain to the effluent; deriving data for the pixels in the picture; and analyzing the data for the pixels that pertain to the effluent to determine the opacity of the effluent.

In accordance with another aspect of this embodiment of the invention, the method further comprises the step of obtaining the picture of the effluent to be analyzed.

In accordance with another aspect of this embodiment of the invention, the obtaining step includes the step of taking pictures with a digital camera.

In accordance with another aspect of this embodiment of the invention, the obtaining step includes the step of scanning a picture with a digital scanner.

In accordance with another aspect of this embodiment of the invention, the picture is converted into a graphics file format.

In accordance with another aspect of this embodiment of the invention, the graphics file format is an JPEG file format.

In accordance with another aspect of this embodiment of the invention, the picture has at least a resolution of 800×600 pixels.

In accordance with another aspect of this embodiment of the invention, the effluent is a smoke plume.

In accordance with another aspect of this embodiment of the invention, the effluent is a dust cloud.

In accordance with another aspect of this embodiment of the invention, the identifying step includes the step of removing artifacts from the picture.

In accordance with another aspect of this embodiment of the invention, the method further comprises the step of selecting a section of the effluent to be analyzed; wherein the identifying and analyzing steps are performed only for the pixels that are included in the selected section.

In accordance with another aspect of this embodiment of the invention, the selected section of the effluent to be analyzed conforms with statutory guidelines governing the selection of a smoke plume to analyze for opacity.

In accordance with another aspect of this embodiment of the invention, the identifying step includes the step of normalizing the data for the pixels.

In accordance with another aspect of this embodiment of the invention, the data comprises color information of the pixels.

In accordance with another aspect of this embodiment of the invention, the data is represented by values in a RGB color space.

In accordance with another aspect of this embodiment of the invention, the color information is represented by values in a HSL color space.

In accordance with another aspect of this embodiment of the invention, the analyzing step comprises the step of performing a principle components analysis on the color information of the pixels.

In accordance with another aspect of this embodiment of the invention, the analyzing step comprises the step of calculating the first principle component of the data of the pixels; and determining the opacity of each pixel pertaining to the cloud by the relationship of each pixel's data to the first principle component.

In accordance with another aspect of this embodiment of the invention, a single opacity value is calculated for the cloud based on the opacity values of the pixels pertaining to the cloud.

In accordance with another embodiment of the invention, an apparatus for evaluating a picture of an effluent to determine the opacity of the effluent comprises a pixel classifier to define pixels of the picture and determine which pixels pertain to the effluent; the pixels having data characterizing the pixels; and a pixel analyzer to process the data for each pixel and calculate the opacity of each the pixel.

In accordance with another aspect of this embodiment of the invention, the pixel analyzer performs a principle components analysis of the data for the pixels to determine the opacity of each pixel pertaining to the effluent.

In accordance with another aspect of this embodiment of the invention, a single opacity value is calculated for the effluent in the picture based on the opacity values of the pixels pertaining to the effluent.

In accordance with another aspect of this embodiment of the invention, the pixel classifier removes artifacts from the picture and normalizes the data for the pixels.

In accordance with another aspect of this embodiment of the invention, the data comprises color information in a color space.

In accordance with another aspect of this embodiment of the invention, the color space is a RGB color space.

In accordance with another aspect of this embodiment of the invention, the pixel classifier and pixel analyzer operate only on a selected portion of the picture.

In accordance with another aspect of this embodiment of the invention, the pixel classifier and pixel analyzer operate on a plurality of pictures; the plurality of pictures depicting the effluent cloud to be analyzed at different times.

In accordance with another aspect of this embodiment of the invention, a single opacity value is calculated for the effluent in each picture based on the opacity values of the pixels pertaining to the effluent in each picture.

In accordance with another aspect of this embodiment of the invention, a total opacity value is calculated for the effluent based on the single opacity values for the effluent in each picture.

In accordance with another embodiment of the invention, a method for reporting the opacity of an effluent comprises the steps of defining pixels of a picture of the pixels of the cloud; calculating the opacity of the pixels of the cloud; grouping the pixels into different groups; the groups corresponding to a different range of opacity values; assigning each group to a different color; and replacing each pixel of the cloud in the picture with colored pixels corresponding to the color assigned to each group.

In accordance with another aspect of this embodiment of the invention, a method wherein the range of opacity values comprise five percentiles.

In accordance with another aspect of this embodiment of the invention, a method wherein the range of opacity values comprise twenty-five percentiles.

DETAILED DESCRIPTION OF DRAWINGS

Figure 1:
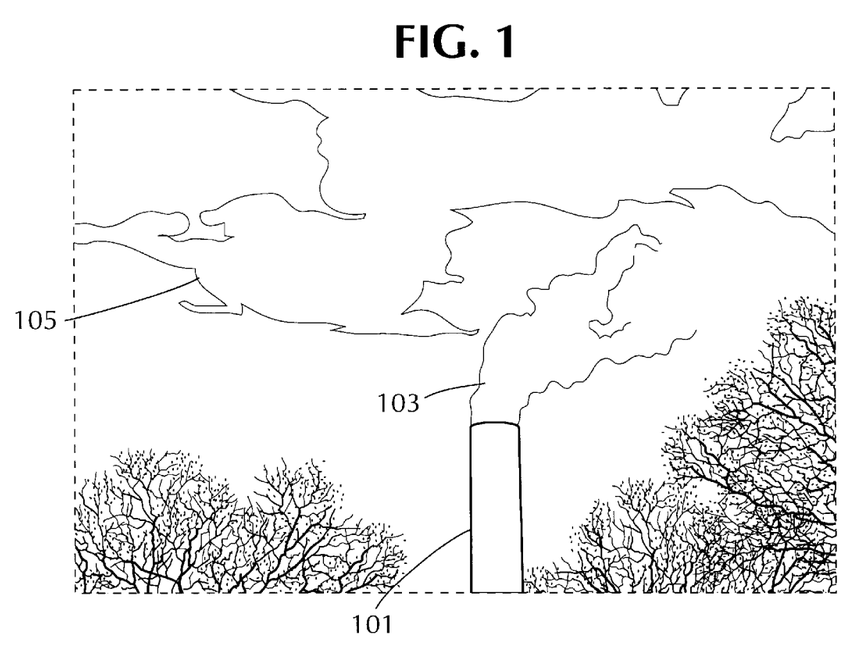
FIG. 1 is a picture which shows a smoke plume to be analyzed under normal conditions.

FIG. 1 shows a picture of a typical smoke plume that needs to be analyzed to determine the opacity level. Although this smoke plume has been frozen in time by the picture, normal human observation require that the judgement of opacity occur while the smoke is still flowing out of the smoke stack.

As seen in FIG. 1, smoke stack 101 is emitting smoke 103 into the atmosphere. The smoke takes on a plume-shaped form and dissipates as it reaches further into the atmosphere.

Also in FIG. 1, several phenomena are shown that need to be discounted by the human observer in calculating the opacity levels. For example, cloud 105 would have to be discounted in analyzing the smoke plume.

Figure 2:
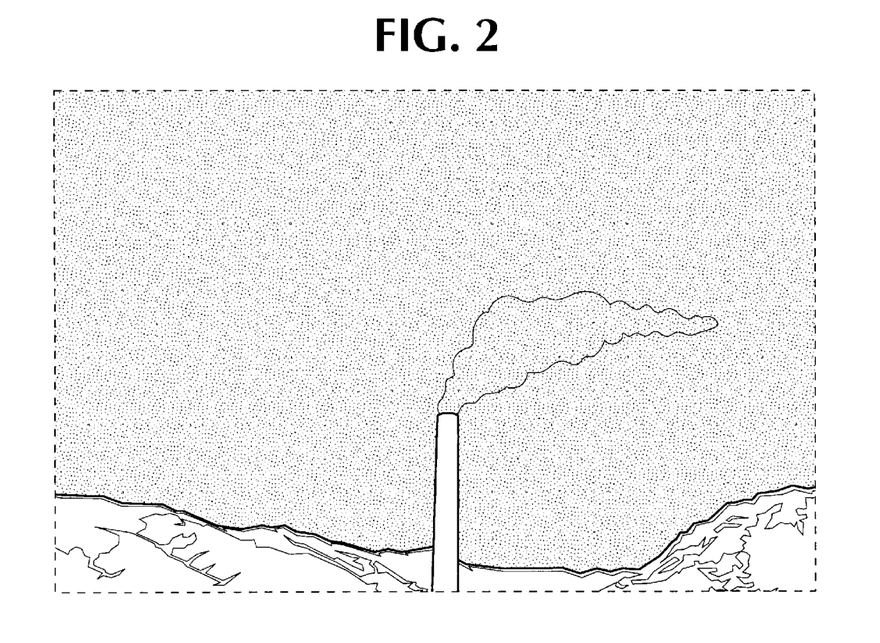
FIG. 2 is a picture which shows a smoke plume to be analyzed under difficult conditions.

Occasionally, the sky background behind the smoke plume can also be different than its normal blue color or other colored objects appear directly behind the smoke plume. These conditions affect the analysis of the smoke plume. FIG. 2 shows such a situation where the background sky is overcast and the color of the sky is similar to the color of the smoke plume. Both smoke plumes in FIGS. 1 & 2 would have to be analyzed.

Figure 3:
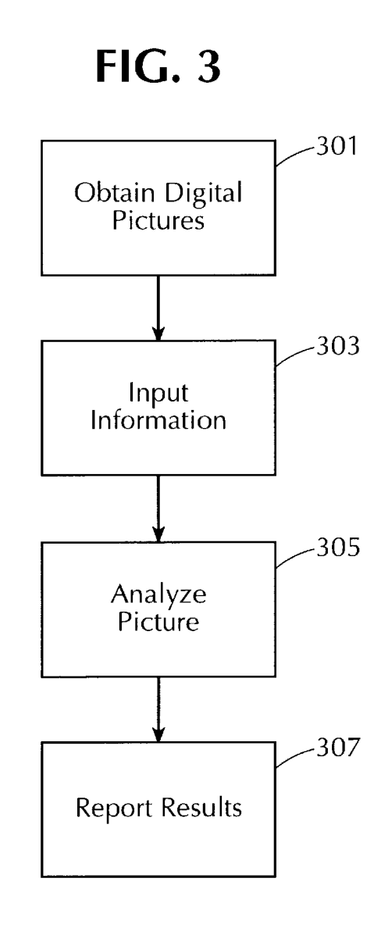
FIG. 3 is a flow chart depicting the operation of one embodiment of the present invention.

FIG. 3 describes the operation of one embodiment of the present invention called the ODECS system. First, the user must take pictures of the smoke plume to be analyzed in the obtaining pictures step 301. As can be seen by FIGS. 1 and 2, the pictures should not focus only on the smoke plume. It should be an accurate representation of the scene as would be seen by an observer. The picture can be taken such that the smoke plume is approximately 10% of the width of the picture. Taking a picture wider than the smoke plume is not only necessary for analysis but gives a frame of reference for the user.

The pictures should be taken in compliance with the statutory regulations that sets guidelines for human observation of smoke plumes. Method 9 specifies that the observer shall stand at a distance sufficient to provide a clear view of the emissions with the sun oriented to his back. Method 9 also states that the observer shall, to the extent possible, make the observations from a position such that his line of vision is approximately perpendicular to the plume direction.

The camera can be situated in a position such that the distance from the smoke plume, the angle of observation and the ambient circumstances of the picture would be identical for both the camera and the human observer. These conditions can be duplicated by setting up the digital camera as though they were the eyes of the human observer. Tripods and other fixing devices can facilitate this duplication.

Pictures can be taken by using a standard or digital camera. If a standard camera is used, the resulting picture must be digitized for analysis. The camera taking the pictures must be able to capture sufficient information in order to perform the plume opacity analysis. The image must have a minimum resolution of 800×600 pixels. A digital camera should also be able to store the pictures as image files. The preferred file format is the JPEG format, but many other image file formats are acceptable.

The JPEG graphic file format can store 24-bit color data per pixel. The JPEG format typically stores the color information of a pixel in 3 discrete values. These values can represent red, green and blue brightness values ("RGB"). For the RGB values, an 8bit value is stored for each primary color and the combination for each primary color value can produce the color spectrum.

The data stored in the JPEG file format can be transformed into values of Hues, Saturation and Luminance ("HSL"). In using the HSL values, hue represents the dominant wavelength of the color, saturation describes how pure the color is and luminance describes the brightness level of the color's brightest RGB component.

The Kodak DC 265 and DC 290 are cameras that are capable of taking the digital pictures with the required resolution and compression. In addition, the DC 265 and 290 cameras are capable of being programmed such that the initial settings of the camera can be predetermined. The settings of the camera, such as the brightness and saturation, can influence the analysis of the digital picture in determining the opacity of the smoke plume. Predetermining the values of the initial settings allows easy calibration of the ODECS system and also provides a check against falsified readings.

Once the digital pictures are taken, the user loads the digital pictures into the ODECS system in the input step 303. In following the statutory regulations, multiple observations for a smoke plume are usually required at distinct time intervals. Method 9 requires that a minimum of 24 distinct observations must be taken at 15 second intervals. As such, for a particular smoke plume, multiple pictures of the smoke plume would usually have to be evaluated. Individual picture files can be evaluated independently or as a series of pictures corresponding to the same smoke plume.

When inputting the digital file into the ODECS system, information regarding the condition surrounding the smoke plume and/or information about the digital picture itself is also entered in the input step 303. Part of this input can include the initial settings of the digital camera. In a preferred embodiment, the initial settings of the camera are set by software scripts provided with the system. Other input to be entered by the user can include the type of smoke plume, the direction of the wind and the start and stop times of the observation.

The user may also be requested to input an estimate of what a 100% opaque plume would look like. This type of input is usually reserved for those situations where a blue sky background is not available. Also as part of the input step 303, the user selects the area of the smoke plume to analyze.

Figure 4:
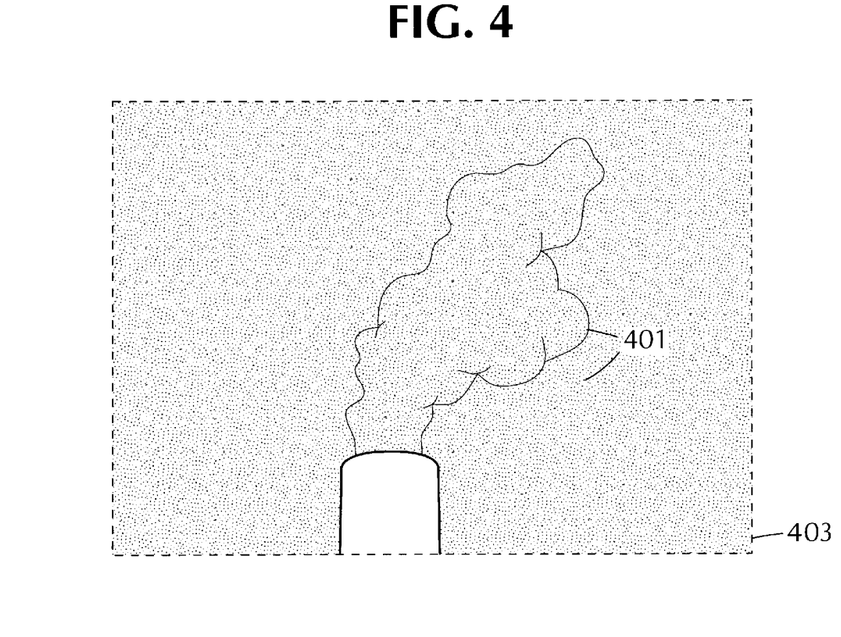
FIG. 4 is a digital picture which shows the selection of the section of the picture to be analyzed.

Referring to FIG. 4, the selected section 401 is indicated by the rectangular box 403. The selected section 401 of the picture should include the background neighboring the smoke plume. As can be seen in FIG. 4, the neighboring background included in the selected section 401 should be similar to the background that is directly behind the smoke plume. By including the neighboring background material as part of the selected section 401 of the picture to analyze, the user allows a reference point against which to analyze the smoke plume.

The selected section 401 should also conform to the guidelines established by the Statutory Regulations. For example, Method 9 dictates that opacity observations should be the point of greatest opacity in that portion of the plume where condensed water vapor is not present. In selecting the section of the picture to analyze under the ODECs system, the user will typically select the section of the plume that is of one-half of the smoke stack width above the smoke stack to two stack widths above the stack by one stack width to the left of the plume to one stack width right of the plume. This section of the plume has been determined to be far enough from the smoke stack to show true opacity and not far enough to allow the smoke to fully dissipate. The sampled area must account for the effects of wind.

Figure 5:
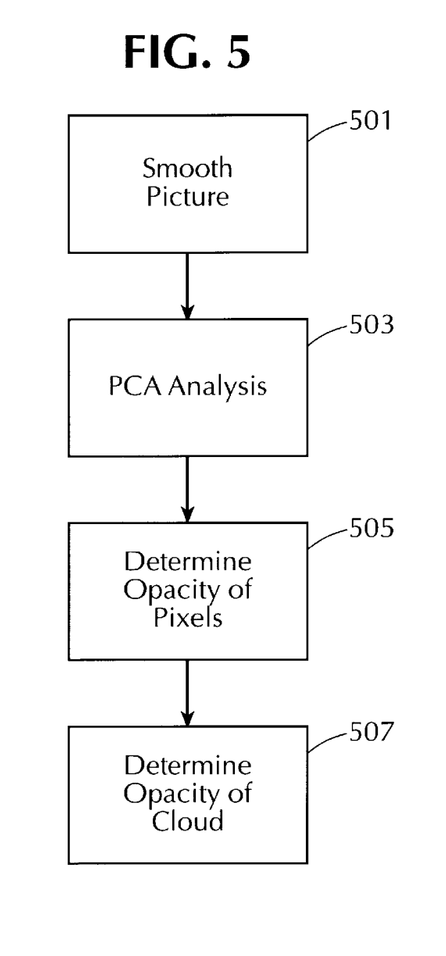
FIG. 5 is a flow chart depicting the operation of one embodiment of the present invention.

After the input step 303, the picture can be broken down into pixels to be analyzed in the picture analysis step 305. FIG. 5 depicts a flow chart which demonstrates the operation of the picture analysis step 305.

The first step 501 in analyzing the picture is to smooth the picture in order minimize the effects of artifacts in the picture. An artifact may be caused by naturally occurring phenomenon or may be mechanically induced during sampling. For example, a scratch in the lens can cause a mark in the picture. This mark will be translated by the digital picture as an object existing in reality when, in fact, it is really an imperfection in the picture.

Other normalizing techniques can be applied as necessary prior to calculating opacity values depending on the complexity of the selected section of the picture. For example, if the background neighboring the smoke plume is not uniform or contains interfering colors from natural objects such as clouds, then these phenomena must be accounted for before analyzing the pixels of the plume. These phenomena will normally be detected when defining the contours of the smoke plume. Once detected, the appropriate interfering phenomena must be distinguished from the smoke plume and discounted by the software or the user intervention.

Detection and discounting of these phenomena can be done by manual intervention by the user. If the user determines that there are interfering phenomena with the select section of the picture, the user can indicate these phenomena instead of relying on automatic detection and discounting.

The ODECS program will then perform the opacity analysis for each pixel of the plume. The analysis of the plume requires a statistical analysis of the RGB information contained in the image file format.

In some cases, it is advantageous to also process the color information in the HSL space because the values for hue and saturation are independent from scene brightness. This independence from scene brightness is used to maintain the calibration of the statistical analysis over a range of scene types. The components of hue and saturation can be used as scaling references in the analysis.

To analyze the smoke plume, a statistical analysis of the RGB information is performed on the area selected by the user. Since each pixel is represented by three variables, namely the RGB values, a principal components analysis ("PCA") is used.

PCA is a multi-variant data analysis that produces a system of orthogonal axis that includes the major axis, the first principal component, of the data distribution. With a PCA, the pixel data of the selected section of the picture can be projected unto an axis relevant to opacity.

Figure 6:
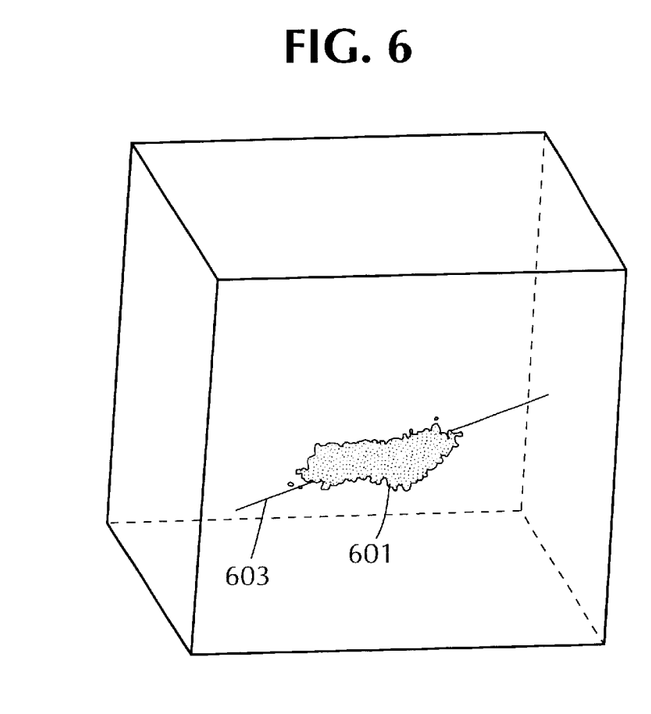
FIG. 6 is a graphical representation of pixels plotted in three dimensional color space and the calculation of the first principal component to these data points.

FIG. 6 depicts a graphical representation of the calculation of the first principle component. Each pixel pertaining to the selected section of the picture is graphed on three axis that correspond the RGB values of the pixels. The distribution of each pixel in this color space essentially creates a distribution of data points 601.

As can be seen in FIG. 6, the first principle component can be graphically depicted as a straight line 603 passing through the cloud of data points. The first principle component essentially represents the line that best fits through the cloud of points and can serve as a standard against which to evaluate the pixels.

After obtaining the first principle component for the data points for the plume, each plume pixel can be evaluated for opacity by its relationship to the first principle component. The first step that needs to be performed is to define the contours of the plume in order to be able to designate those pixels of the picture as plume pixels which need to be evaluated for opacity. After that, the opacity of the smoke plume pixels is calculated as a function of their displacement along the first principle component axis.

Assigning individual opacity values to each pixel, however, does not evaluate the opacity of the smoke plume on a whole. A single value for the opacity of the entire plume can be extrapolated through a histogram analysis of opacity values over the sample. While a single value can be useful, it is also helpful to group the pixels into groups of incremental opacity levels. In the preferred embodiment, pixels are sorted into the opacity levels of 5% increments for the first 50 percentiles and 25% increments for the latter 50 percentiles that correspond to the guidelines established under Method 9 . Sorting the smoke plume pixels into these incremental groups allows for a quick look determination of the preponderant opacity value in addition to the single-derived opacity value.

Figure 7:
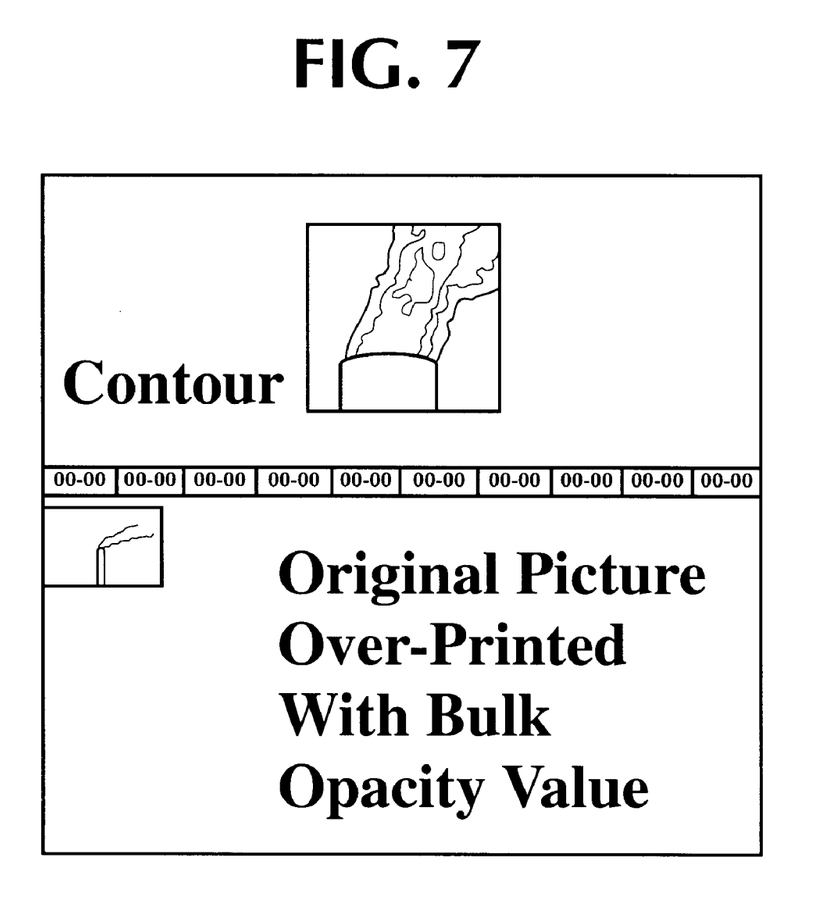
FIG. 7 is a contour plot of a sample smoke plume.

Graphing these results in a contour plot can also be useful in a analysis of the effects of process changes on the resultant effluent. FIG. 7 depicts one such contour plot. As can be seen in FIG. 7, the shape of the smoke plume is accurately reproduced with the sections of the smoke plume replaced by color coded to represent a different opacity interval.

Figure 8:
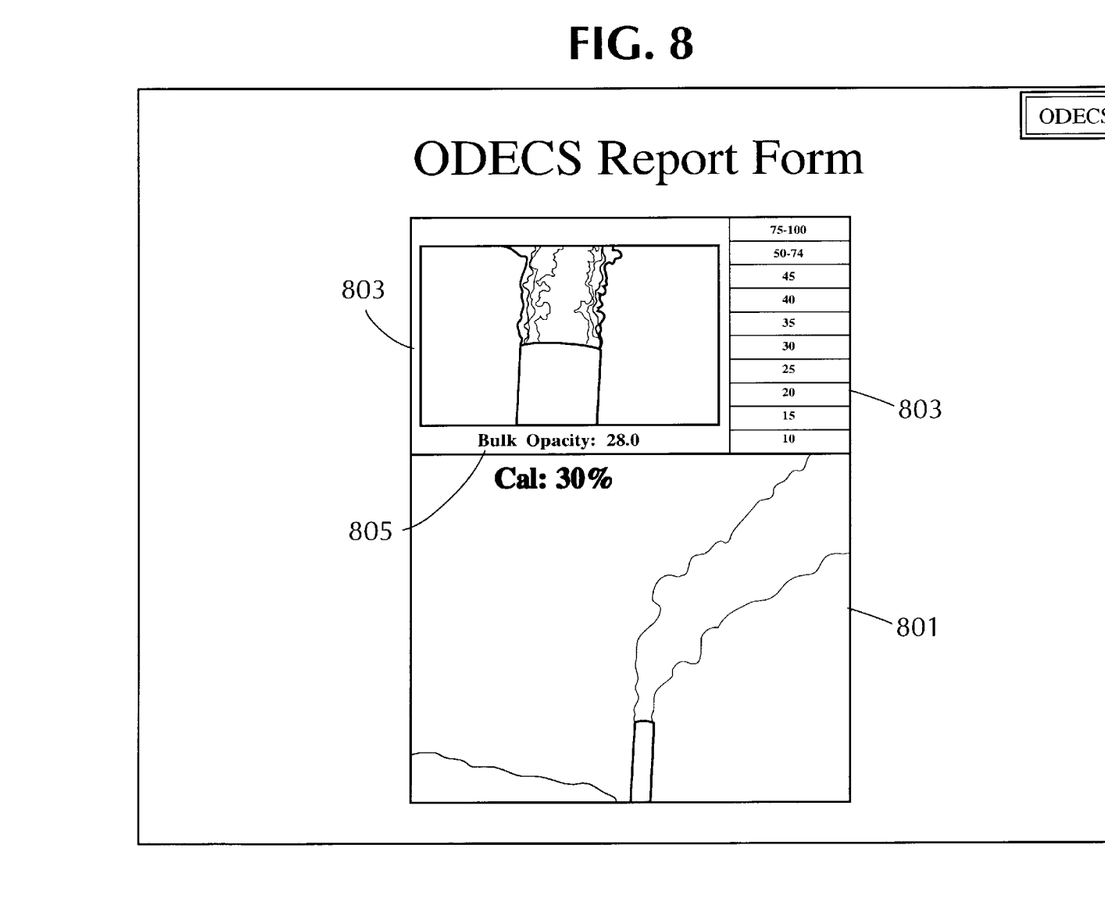
FIG. 8 is one embodiment of a report presenting the results of the opacity analysis.

After the smoke plume has been analyzed and the opacity values determined, the results in opacity calculations can be presented to the user in various forms. Both the single opacity value and the contour plot are be presented to the user for any individual smoke plume as seen in FIG. 8. In FIG. 8 the picture of the smoke plume 801 is presented below the contour map 803 and the final opacity measurement 805.

Figure 9:
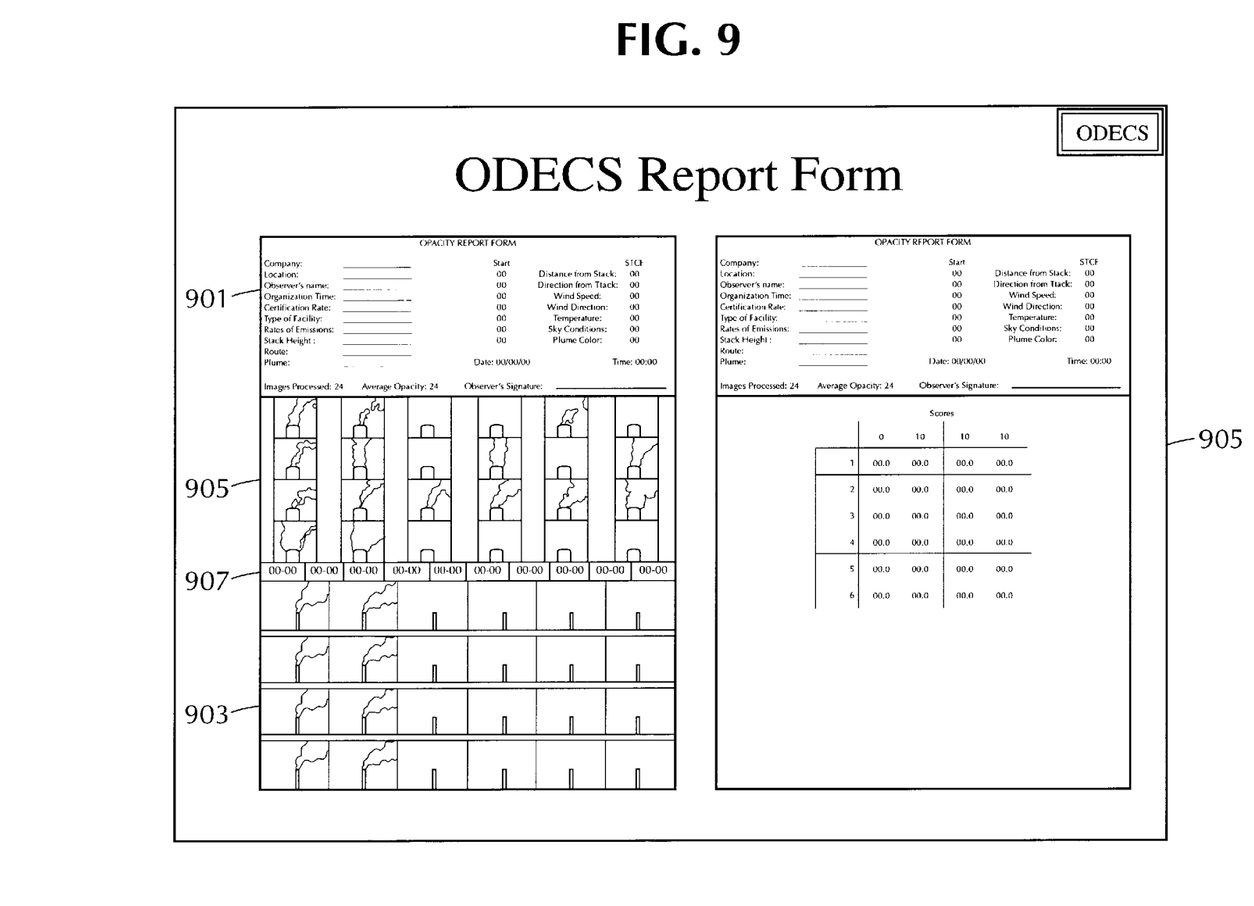
FIG. 9 is another embodiment of a report showing the results of the opacity analysis.

Since typical opacity measurements of a smoke plume require continuous measurements of the same smoke plume for a defined interval of time, it can be useful to group these time delayed measurements together. FIG. 9 depicts one such report form. In that report, a table 901 containing the information input by the user pertaining to that smoke plume is reprinted. The information contained in that table can include identification of that smoke stack owner, times of the observation and the ambient weather conditions.

The pictures 903 used in the measurement of the opacity of the smoke plume are reproduced with the opacity reading for each individual picture superimposed on the picture. The report also includes the contour plot 905 for each individual picture. The common legend 907 mapping the color codes to the various opacity intervals is displayed along with the contour plots 905. The results of all the individual opacity measurements can be presented in tabular format 909 as well to correlate the times of each observation with the opacity of the plume. Grouping the pictures corresponding to the same smoke plume allows calculation of one single opacity value of the smoke plume for the period of observation. The final opacity measurement can be a straight average or a weighted average of the individual opacity values.

As discussed above, the ODECS system is applicable to measuring the opacity of the smoke plumes. The ODECS system is equally applicable to other situations in which a opacity reading is desired. For example, fugitive dust is an environmental concern that can be subject to regulation. Fugitive dust is a general term to describe clouds of dust particles that are airborne. Measuring the amount of fugitive dust in a given area would require a measurement of the opacity of the dust cloud.

Figure 10:
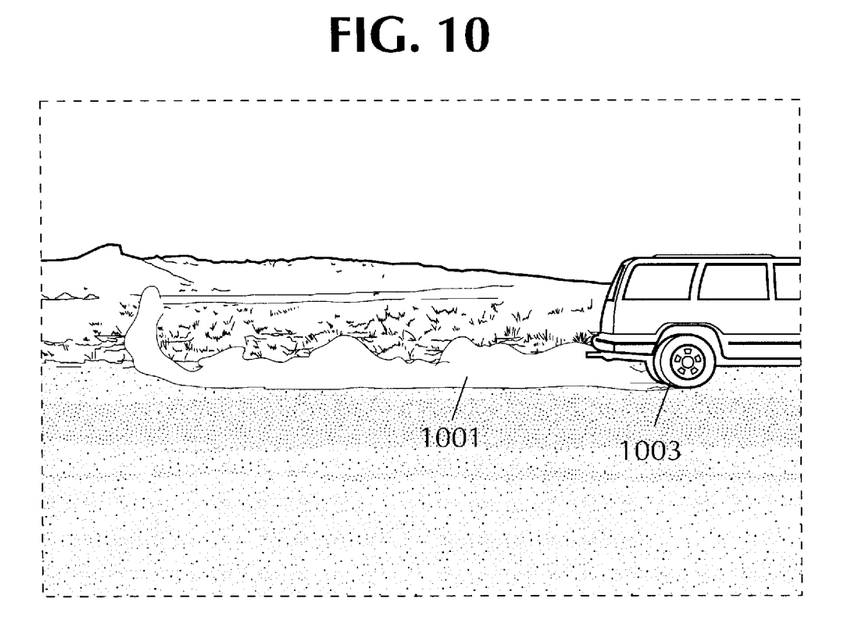
FIG. 10 is a pictorial representation of a another application for the present invention involving the analysis of fugitive dust situation wherein a fugitive of dust exists.

The same basic approach used by the ODECS system in analyzing the smoke plume is applicable in measuring fugitive dust. FIG. 10 depicts a picture of a situation in which a dust cloud 1001 is created by a automobile 1003 passing through a dusty area. Similar to the smoke plume created by a smoke stack, dust cloud 1001 can be isolated in the picture and analyzed for the opacity of the dust cloud.

While ODECS uses the PCA to determine opacity plumes against a fairly uniform background, e.g. the sky, provision is also made for determining opacity of an effluent, such as a dust cloud, against a complex background. In the later case, prevalent in sampling dust clouds, a different analysis is performed. In complex background analysis, spatial characteristics rather than color characteristics become the focus. Data used are present in the image file, just as they are in the plume analysis; however, comparison is made of the entire image, rather than of a user selected portion of the image. To do a complex background(dust)analysis, the user takes an image of the area of interest in its normal state, that is with no dust plume. A second, or series of additional images are taken to be analyzed. Image data are then compared using spatial characteristics of the image, represented by grouped pixels. Characteristics such as clarity, edge definition, frequency and position of image contours are determined from the 'clean image' and compared with those of sample images.

The change in spatial characteristics between the two images is then translated into a quantification of opacity. In other words, loss of definition in the image is interpreted as opacity. Values of these opacity levels are then presented over the sample image in the same manner as described under plume contouring.

Figure 11:
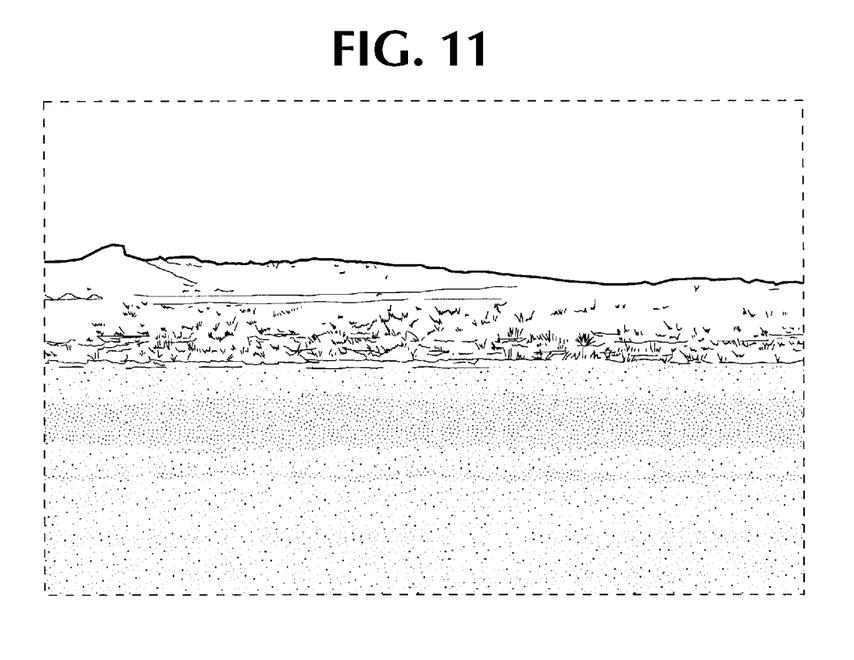
FIG. 11 is a pictorial representation of a situation wherein fugitive dust can occur.

FIG. 11 depicts a picture of the same location as the picture of FIG. 10, but without the automobile and without the dust cloud. By comparing the pixels of one picture against the corresponding pixels of the other picture, the ODECS system can accurately measure the opacity of each pixel of the dust cloud. This measurement still requires an analysis of the pixels of the pictures, but it is not as complex as the analysis for the continuous smoke plume.

The present invention is not to be considered limited in scope by the preferred embodiments described in the specification. Additional advantages and modifications, which readily occur to those skilled in the art from consideration and specification and practice of this invention are intended to be within the scope and spirit of the following claims.

We claim:

1. A method for evaluating a picture of an effluent to determine the opacity of said effluent, comprising the steps of:
   identifying pixels in said picture that pertain to said effluent;
   deriving data for said pixels in said picture; and
   analyzing said data for said pixels that pertain to said effluent to determine the opacity of said effluent.

2. A method as claimed in claim 1, further comprising the step of obtaining said picture of said effluent to be analyzed.

3. A method as claimed in claim 2, wherein said obtaining step includes the step of taking pictures with a digital camera.

4. A method as claimed in claim 2, wherein said obtaining step includes the step of scanning a picture with a digital scanner.

5. A method as claimed in claim 1, wherein said picture is converted into a graphics file format.

6. A method as claimed in claim 5, wherein said graphics file format is a JPEG file format.

7. A method as claimed in claim 1, wherein said picture has at least a resolution of 800×600 pixels.

8. A method as claimed in claim 1, wherein said effluent is a smoke plume.

9. A method as claimed in claim 1, wherein said effluent is a dust cloud.

10. A method as claimed in claim 1, wherein said identifying step includes the step of removing artifacts from said picture.

11. A method as claimed in claim 1, further comprising the step of selecting a section of said effluent to be analyzed; wherein said identifying and analyzing steps are performed only for the pixels that are included in said selected section.

12. A method as claimed in claim 11, wherein said selected section of said effluent to be analyzed conforms with statutory guidelines governing the selection of a smoke plume to analyze for opacity.

13. A method as claimed in claim 1, wherein said identifying step includes the step of normalizing said data for said pixels.

14. A method as claimed in claim 13, wherein said data comprises color information of said pixels.

15. A method as claimed in claim 14, wherein said data is represented by values in a RGB color space.

16. A method as claimed in claim 1, wherein said color information is represented by values in a HSL color space.

17. A method as claimed in claim 14, wherein said analyzing step comprises the step of performing a principle components analysis on said color information of said pixels.

18. A method as claimed in claim 11, wherein said analyzing step comprises the step of calculating the first principle component of said data of said pixels; and determining the opacity of each pixel pertaining to said cloud by the relationship of each pixel's data to said first principle component.

19. A method as claimed in claim 18, wherein a single opacity value is calculated for said cloud based on the opacity values of the pixels pertaining to said cloud.

20. An apparatus for evaluating a picture of an effluent to determine the opacity of said effluent, said apparatus comprising:
   a pixel classifier to define pixels of said picture and determine which pixels pertain to said effluent; said pixels having data characterizing said pixels;
   a pixel analyzer to process said data for each pixel and calculate the opacity of each said pixel.

21. An apparatus as claimed in claim 20, wherein said pixel analyzer performs a principle components analysis of the data for said pixels to determine the opacity of each pixel pertaining to said effluent.

22. An apparatus as claimed in claim 21, wherein a single opacity value is calculated for said effluent in said picture based on the opacity values of the pixels pertaining to said effluent.

23. An apparatus as claimed in claim 20, wherein said pixel classifier removes artifacts from said picture and normalizes said data for said pixels.

24. An apparatus as claimed in claim 20, wherein said data comprises color information in a color space.

25. An apparatus as claimed in claim 24, wherein said color space is a RGB color space.

26. An apparatus as claimed in claim 20, wherein said pixel classifier and pixel analyzer operate only on a selected portion of said picture.

27. An apparatus as claimed in claim 20, wherein said pixel classifier and pixel analyzer operate on a plurality of pictures; said plurality of pictures depicting said effluent cloud to be analyzed at different times.

28. An apparatus as claimed in claim 27, wherein a single opacity value is calculated for said effluent in each picture based on the opacity values of said pixels pertaining to said effluent in each picture.

29. An apparatus as claimed in claim 27, wherein a total opacity value is calculated for said effluent based on the single opacity values for said effluent in each picture.

30. A method for reporting the opacity of a effluent, comprising the steps of:

defining pixels of a picture of said pixels of said cloud;

calculating the opacity of said pixels of said cloud;

grouping said pixels into different groups; said groups corresponding to a different range of opacity values;

assigning each group to a different color; and replacing each pixel of said cloud in said picture with colored pixels; said colored pixels corresponding to the color assigned to each group.

31. A method as claimed in claim 30, wherein said range of opacity values comprise twenty five percentiles.

\* \* \* \* \*